(12) United States Patent
'T Hooft et al.

(10) Patent No.: US 9,341,569 B2
(45) Date of Patent: May 17, 2016

(54) METHOD FOR DETECTING THE PRESENCE OF INHOMOGENEITIES IN AN INTERIOR OF A TURBID MEDIUM AND DEVICE FOR IMAGING THE INTERIOR OF TURBID MEDIA

(75) Inventors: Gert 'T Hooft, Eindhoven (NL); Martinus Bernardus Van Der Mark, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1211 days.

(21) Appl. No.: 12/747,179

(22) PCT Filed: Dec. 11, 2008

(86) PCT No.: PCT/IB2008/055226
§ 371 (c)(1),
(2), (4) Date: Sep. 8, 2010

(87) PCT Pub. No.: WO2009/077947
PCT Pub. Date: Jun. 25, 2009

(65) Prior Publication Data
US 2010/0331705 A1 Dec. 30, 2010

(30) Foreign Application Priority Data
Dec. 17, 2007 (EP) .................................. 07123319

(51) Int. Cl.
*A61B 5/05* (2006.01)
*G01N 21/47* (2006.01)
*A61B 5/00* (2006.01)
*G01N 21/64* (2006.01)

(52) U.S. Cl.
CPC .......... *G01N 21/4795* (2013.01); *A61B 5/0091* (2013.01); *A61B 5/4312* (2013.01); *G01N 21/6456* (2013.01)

(58) Field of Classification Search
USPC ......... 600/407, 425, 431, 437, 458, 473, 476; 356/3.01, 3.02, 3.12, 4.01, 432, 433; 356/435; 250/578.1
See application file for complete search history.

(56) References Cited

U.S. PATENT DOCUMENTS 5,719,398 A * 2/1998 Colak .................... 250/341.1
5,722,406 A * 3/1998 Papaioannou ............... 600/407
(Continued)

FOREIGN PATENT DOCUMENTS

WO 2007060586 A2 5/2007

OTHER PUBLICATIONS

Boas, D.: "Quantitative Diffuse Optical Tomography Requires Non-linear Reconstruction Algorithms"; Conference on Lasers and Electro-Optics, 1998, CLEO '98 Technical Digest, pp. 87-88.
(Continued)

*Primary Examiner* — James Kish
*Assistant Examiner* — Michael N Fisher

(57) ABSTRACT

A method includes performing first and second measurements with a turbid medium to be examined placed in a receiving volume of a device for examining the interior of turbid media. The second measurement is performed after a time interval has passed after the first measurement. Each of the first and second measurements includes subsequently irradiating the turbid medium with light from a light source from a plurality of different source positions and detecting light emanating from the turbid medium in a plurality of different detection positions for each source position, and storing the detected values as measurement results. The method also includes detecting inhomogeneities in the interior of the turbid medium by using the measurement results of one of the first and second measurements as a reference and the measurement results of the respective other of the first and second measurements to determine deviations from the reference.

10 Claims, 2 Drawing Sheets

(56) References Cited

U.S. PATENT DOCUMENTS

| | | | |
|---|---|---|---|
| 5,907,406 A * | 5/1999 | Papaioannou et al. | 356/432 |
| 6,023,341 A * | 2/2000 | Colak | 356/435 |
| 6,064,073 A * | 5/2000 | Hoogenraad | 250/573 |
| 6,064,917 A * | 5/2000 | Matson | 700/90 |
| 6,091,983 A * | 7/2000 | Alfano et al. | 600/431 |
| 6,230,045 B1 | 5/2001 | Hoogenraad et al. | |
| 6,240,309 B1 * | 5/2001 | Yamashita et al. | 600/407 |
| 6,415,172 B1 * | 7/2002 | Painchaud et al. | 600/407 |
| 6,480,281 B1 * | 11/2002 | Van Der Mark et al. | 356/432 |
| 6,640,133 B2 * | 10/2003 | Yamashita et al. | 600/476 |
| 6,671,540 B1 * | 12/2003 | Hochman | 600/431 |
| 6,687,532 B2 * | 2/2004 | Ohmae et al. | 600/425 |
| 7,006,676 B1 * | 2/2006 | Zeylikovich et al. | 382/131 |
| 7,046,832 B1 * | 5/2006 | Barbour | 382/131 |
| 2004/0039268 A1 * | 2/2004 | Barbour et al. | 600/310 |
| 2004/0073101 A1 * | 4/2004 | Chance | 600/322 |
| 2005/0085732 A1 * | 4/2005 | Sevick-Muraca et al. | 600/473 |

OTHER PUBLICATIONS

Boas, D.: "A Fundametnal Limitation of Linearized Algorithms for Diffuse Optical Tomography"; Optics Express, Dec. 1997, vol. 1, No. 13, pp. 404-413.

Ntziachristos, V.: "Concurrent Diffuse Optical Tomography, Spectroscopy and Magnetic Imaging of Breast Cancer"; A Dissertation in Bioengineering, University of Pennsylvania, 2000, pp. 93-127.

Wasserman, B.: "Limits of High-Order Perturbation Theory in Time-Domain Optical Mammography"; Physical Review, vol. E74, No. 031098, 2006, pp. 031908-1-031908-13.

Grosenick et al:: "Evaluation of Higher-Order Time-Domain Perturbation Theory of Photon Diffusion on Breast-Equivalent Phantoms and Optical Mammograms"; Physical Review E76, vol. 061908, 2007, pp. 061908-1-061908-18.

Hoogenraad et al: "First Results From the Philips Optical Mammoscope"; SPIE, vol. 3194, 1998, pp. 184-190.

Colak et al: "Tomographic Image Reconstruction From Optical Projections in Light-Diffusing Media"; Applied Optics, vol. 36, No. 1, Jan. 1997, pp. 180-213.

Hoogenraad et al: "First Results From the Philips Optical Mammoscope"; Photon Propagation in Tissues III, SPIE, vol. 3194, 1997, pp. 184-190.

Colak et al: "Clinical Optical Tomography and NIR Spectroscopy for Breast Cancer Detection"; IEEE Journal of Selected Topics in Quantum Electronics, vol. 5, No. 4, Jul./ Aug. 1999.

* cited by examiner

METHOD FOR DETECTING THE PRESENCE OF INHOMOGENEITIES IN AN INTERIOR OF A TURBID MEDIUM AND DEVICE FOR IMAGING THE INTERIOR OF TURBID MEDIA

FIELD OF INVENTION

The present invention relates to a method for detecting the presence of inhomogeneities in an interior of a turbid medium and to a device for imaging the interior of turbid media which is adapted accordingly.

BACKGROUND OF THE INVENTION

In the context of the present application, the term turbid medium is to be understood to mean a substance consisting of a material having a high light scattering coefficient, such as for example an intralipid solution or biological tissue. Further, light is to be understood to mean electromagnetic radiation of a wavelength in the range from 400 nm to 1400 nm. The term "optical properties" covers the reduced scattering coefficient $\mu'_s$ and the absorption coefficient $\mu_a$. Furthermore, "matching optical properties" is to be understood as having a similar reduced scattering coefficient $\mu'_s$ and a similar absorption coefficient $\mu_a$.

In recent years, several methods and devices for examining turbid media, e.g. female breast tissue, have been developed. In particular, new devices for detection and analysis of breast cancer have been developed and existing technologies have been improved. Breast cancer is one of the most occurring types of cancer: in 2002, for example, more than 1.1 million women were diagnosed and over 410,000 women died of breast cancer world-wide. Several types of devices for imaging the interior of a turbid medium by use of light have been developed. Examples for such devices are mammography devices and devices for examining other parts of human or animal bodies. A prominent example for a method for imaging the interior of a turbid medium is Diffuse Optical Tomography (DOT). In particular, such devices are intended for the localization of inhomogeneities in in vivo breast tissue of a part of a breast of a female human body. A malignant tumor is an example of such an inhomogeneity. The devices are intended to detect such inhomogeneities while they are still small, so that for example carcinoma can be detected at an early stage. A particular advantage of such devices is that the patient does not have to be exposed to the risks of examination by means of ionizing radiation, as e.g. X-rays. Furthermore, X-ray based equipment have a limited detectability and sensitivity.

U.S. Pat. No. 5,907,406 discloses a device for imaging the interior of a turbid medium by using a light source to irradiate the turbid medium and photodetectors for measuring a part of the light transported through the turbid medium. A control unit is provided for reconstructing an image of the interior of the turbid medium on the basis of the measured intensities. The disclosed device is particularly adapted for examining female breasts. In order to allow the examination of the turbid medium, the device is provided with a receptacle as a receiving volume enclosing a measuring volume and arranged to receive the turbid medium. Light from the light source is coupled into the receiving volume and into the turbid medium. The light is chosen such that it is capable of propagating through the turbid medium. For imaging an interior of a female breast, light having a wavelength within a range of 400 nm to 1400 nm is typically used. Scattered light emanating from the turbid medium as a result of coupling light into the receiving volume is coupled out of the receiving volume. Light coupled out of the receiving volume is used to reconstruct an image of an interior of the turbid medium. The light used for examining the turbid medium has to be transmitted from the light source to the turbid medium and from the turbid medium to the photodetectors. Due to different sizes of the turbid media to be examined, the size of the receptacle for receiving the turbid medium does not perfectly match the size of the turbid medium, i.e. a space remains between the receptacle and the turbid medium. The part of the turbid medium under investigation is surrounded by a matching medium filling the space in the receiving volume. The matching medium is chosen such that the optical parameters of the matching medium, such as the absorption and scattering coefficients, are substantially identical to the corresponding optical parameters of the turbid medium. In this way, image artifacts resulting from optical boundary effects that occur when light is coupled into and out of the turbid medium can be reduced. Furthermore, use of the matching medium prevents the occurrence of an optical short-circuit in the receiving volume around the turbid medium. An optical short-circuit occurs when light is detected that has propagated along a path inside the receiving volume but outside the turbid medium and, as a consequence, has not been sufficiently scattered and attenuated. In that case the intensity of the insufficiently scattered and attenuated detected light may dwarf the intensity of detected light that has been scattered and attenuated through passage through the turbid medium. The light source subsequently irradiates the turbid medium from different directions and the photodetectors measure a part of the light transmitted through the turbid medium. A plurality of such measurements are performed with the light directed to the turbid medium from different directions and, based on the results of the measurements, i.e. the obtained data set, the control unit reconstructs the image of the examined turbid medium.

In such devices, the image of the interior of the turbid medium under investigation is typically constructed by e.g. filtered backprojection or an algebraic reconstruction technique. Details on reconstruction with filtered backprojection are disclosed in "Tomographic image reconstruction from optical projections in light-diffusing media", Appl. Optics 36, 180 (1997), for example. Information on an algebraic reconstruction technique used for optical mammography is disclosed in "First results from the Philips Optical Mammoscope" in "Photon Propagation in Tissues III", Proc. SPIE Vol. 3194, 184 (1997), for example.

New approaches for further enhancing the accuracy of methods for detecting breast cancer by use of light have been made. For example, a fluorescent dye has been developed which can be used as a fluorescent contrast agent. For this purpose it can be injected into the body and will accumulate in cancer cells. If this fluorescent contrast agent then becomes excited with light of a suitable wavelength, the locally emitted light can be detected. Based on the emitted light, size and localization of carcinoma can be determined. Thus a powerful method for detection and localization of breast cancer is provided. In this case, for reconstructing an image of the interior of the examined turbid medium from the plurality of measurements, the spatial distribution of the fluorescent contrast agent in the interior of the turbid medium has to be reconstructed.

In known methods for reconstructing an image of the turbid medium under investigation, a reference measurement is performed before the actual measurement. In this reference measurement, the receiving volume for receiving the turbid medium during examination, having for example a cup-like shape, is completely filled with the matching medium. Then a complete reference measurement is performed in which a set of data is generated. Thereafter, the turbid medium to be examined, for example a female human breast, is placed in the receiving volume and immersed in the matching medium. The actual measurement ihoi terugs then performed in which a set of data corresponding to that of the reference measurement is generated. The set of data generated during the reference measurement is used as a reference for the set of data generated during the actual measurement. For the purpose of the reconstruction process, it is then assumed that structures inside the examined turbid medium only constitute small deviations from the homogenous matching medium, e.g. a matching fluid, which has been used during the reference measurement. Based on this assumption, in the known methods the image of the interior of the turbid medium is then reconstructed using perturbation theory with linear approximation, since the deviations from the homogenous matching medium are treated as small perturbations to the homogenous matching medium.

However, it has been found that the linear approximation is not generally valid between first measurements with only the optically matching medium and second measurements with the turbid medium immersed in the matching medium. Therefore, the reconstruction achieved using this linear approximation does not always provide satisfactory results.

SUMMARY OF THE INVENTION

It is an object of the present invention to provide a method and a device which allow detecting the presence of inhomogeneities in the interior of a turbid medium with satisfactory accuracy using linear approximation.

This object is solved by a method according to claim 1. A method for detecting the presence of inhomogeneities in an interior of a turbid medium is provided. The method comprises the steps: performing a first measurement with the turbid medium to be examined placed in a receiving volume of a device for examining the interior of turbid media; performing a second measurement with the turbid medium to be examined placed in the receiving volume of the device for examining the interior of turbid media; wherein the second measurement is performed after a time interval has passed after the first measurement. Each of the first and second measurements comprise: subsequently irradiating the turbid medium with light from at least one light source from a plurality of different source positions and detecting light emanating from the turbid medium in a plurality of different detection positions for each source position, and storing the detected values as measurement results. The method further comprises the step: detecting the presence of inhomogeneities in the interior of the turbid medium by using the measurement results of one of the first and second measurements as a reference and the measurement results of the respective other of the first and second measurements to determine deviations from the reference.

By making the second measurement after a time interval has passed after the first measurement, two substantially identical measurements are performed and slight deviations in the structures in the turbid medium will have occurred between the first and second measurements. These deviations will be only small and thus the assumptions for linear approximation will be valid. As a result, inhomogeneities in the interior of the examined turbid medium can be localized with satisfactory accuracy using linear approximation. The first and second measurements are performed with the same setup of turbid medium and receiving volume and corresponding sets of data are generated in the first measurement and in the second measurement.

Preferably, a multiplier is computed for detecting the presence of inhomogeneities, and computing the multiplier includes, for each combination of source position and detection position, computing the ratio between the measurement result from one of the first and second measurements and the corresponding measurement result from the respective other of the first and second measurements. When the multiplier is computed, deviations in the turbid medium which occur in the second measurement with respect to the first measurement can be easily identified. The equations for reconstructing an image of the interior of the turbid can be linearized.

According to an aspect, an averaged term <M> is computed according to the equation:

$$\langle M \rangle = \frac{1}{N} \sum_n \frac{\Phi_n(t_1)}{\Phi_n(t_2)}$$

with N being the number of different combinations of source position and detection position, n being an index for specific combinations of source position and detection position, $\Phi$ being the detected photon density, $t_1$ being the time of the first measurement, and $t_2$ being the time of the second measurement. In this case, a normalized merit function with only small deviations from zero can be easily computed based on the averaged term. Thus, linear perturbation theory can be applied and leads to satisfactory results.

Preferably, an image of the interior of the turbid medium is reconstructed based on the measurement results of the first and second measurements.

Using a first order Born approximation for reconstructing the image of the interior of the turbid medium is very attractive from a computational point of view, since the required computations can be easily implemented.

Preferably, the presence of an inhomogeneity is detected by generating a histogram based on the measurement results of the first and second measurements. In this case, the presence and localization of inhomogeneities can be detected even without or before reconstructing an image of the interior of the turbid medium.

According to an aspect, the first measurement and the second measurement are performed over a time interval where an oxygenation level and/or blood content in the turbid medium has changed owing to a variation in applied pressure or owing to differences within an inhale/exhale breathing cycle. Thus, two measurements fulfilling the assumptions for a linear approach can be provided in a convenient way.

According to an aspect, a contrast agent is injected into the turbid medium before the first measurement is performed. The time interval between the first and second measurements is chosen to be in the order of a decay time of the contrast agent. In this case, the occurrence of non-average wash-out times of the contrast agent can be identified which helps identifying diseased tissue.

The object is further solved by a device for detecting the presence of inhomogeneities in the interior of turbid media according to claim 9. The device comprises: a receiving volume for receiving a turbid medium to be examined; at least one light source for irradiating an interior of the receiving volume; at least one detector for detecting light emanating from the interior of the receiving volume; and a control unit for controlling the device for imaging the interior of turbid media. The control unit is adapted to control the device for imaging the interior of turbid media such that: a first measurement with a turbid medium placed in the receiving volume is performed, and a second measurement with the turbid medium placed in the receiving volume is performed after a time interval has passed after the first measurement. In each of the first and second measurements the turbid medium is subsequently irradiated with light from the at least one light source from a plurality of different source positions and, for each source position, light emanating from the turbid medium is detected in a plurality of different detection positions by the at least one detector, and the detected values are stored as measurement results. The control unit is further adapted such that: the presence of inhomogeneities in the interior of the turbid medium is detected by using the measurement results of one of the first and second measurements as a reference and the measurement results of the respective other of the first and second measurements to determine deviations from the reference. Since the control unit is adapted such that the second measurement is performed after a time interval has passed after the first measurement, two substantially identical measurements are performed and slight deviations in the structures in the turbid medium will have occurred between the first and second measurements. These deviations will be only small and thus the assumptions for linear approximation will be valid. As a result, inhomogeneities in the interior of the examined turbid medium can be detected and localized with satisfactory accuracy using linear approximation.

According to an aspect, the control unit is adapted such that a multiplier is computed for detecting the presence and localizing the position of inhomogeneities, and computing the multiplier includes, for each combination of source position and detection position, computing the ratio between the measurement result from one of the first and second measurements and the corresponding measurement result from the respective other of the first and second measurements.

Preferably, the control unit is adapted such that an averaged term is computed according to the equation:

$$\langle M \rangle = \frac{1}{N} \sum_n \frac{\Phi_n(t_1)}{\Phi_n(t_2)}$$

with N being the number of different combinations of source position and detection position, n being an index for specific combinations of source position and detection position, $\Phi$ being the detected photon density, $t_1$ being the time of the first measurement, and $t_2$ being the time of the second measurement.

According to another aspect, the control unit is adapted such that an image of the interior of the turbid medium is reconstructed based on the measurement results of the first and second measurements.

Preferably, the control unit is adapted to provide a histogram based on the measurement results of the first and second measurements for detecting the presence of inhomogeneities.

Preferably, the device is medical image acquisition device.

Preferably, the position of inhomogeneities is localized

BRIEF DESCRIPTION OF THE DRAWINGS

Further features and advantages of the present invention will arise from the detailed description of embodiments with reference to the enclosed drawings.

DETAILED DESCRIPTION OF EMBODIMENTS

Figure 1:
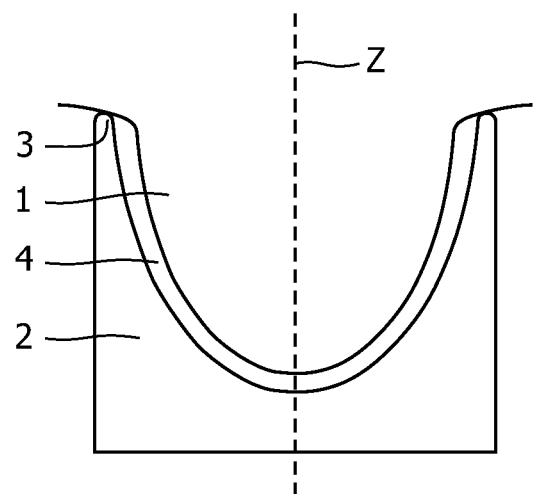
FIG. 1 schematically shows a receptacle of a device for imaging the interior of turbid media.
Figure 2:
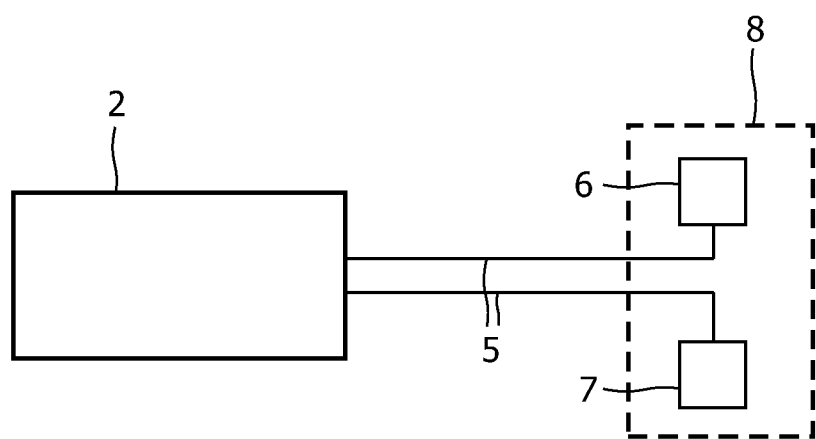
FIG. 2 schematically shows the optical connection between the receptacle and a control unit in the device for imaging the interior of turbid media.

Embodiments of the present invention will now be described with reference to FIGS. 1 and 2. In the embodiments, the device for imaging the interior of a turbid medium is formed by a device for diffuse optical tomography (DOT), in particular by a mammography device. Since the overall construction of such a device is known to a skilled person, no detailed description of the device will be given.

In the device of the embodiments, the turbid medium 1 to be examined is a female human breast. The device is provided with a receptacle 2 (receiving volume) enclosing a measuring volume and arranged to receive the turbid medium 1, as schematically indicated in FIG. 1. The receptacle 2 has a cup-like shape with rotational symmetry with respect to a vertical axis Z and is provided with an opening 3. As can be seen in FIG. 1, the turbid medium 1 to be examined, i.e. the breast, is placed in the receptacle 2 such that it freely hangs in the receptacle 2 from the side of the opening 3. The inner surface of the receptacle facing the turbid medium 3 is provided with a plurality of ends of light guides 5 formed by optically guiding fibers connecting to a light source 6 and to a plurality of detectors 7. These ends of the light guides 5 are distributed on the inner surface of the receptacle 2 such that the receptacle 2 provided with the light guides 5 still comprises substantially rotational symmetry.

The device is further structured such that light from the light source 6 can be directed to the turbid medium 1 from different directions and light emanating from the turbid medium 1 can be detected by a plurality of detectors 7 the corresponding light guides 5 of which are distributed on the inner surface of the receptacle 2. The device comprises a control unit 8 which reconstructs an image of the interior of the turbid medium 1 based on the signals from the detectors 7. For reconstruction, the signals sampled during a scan in which the light is directed to the turbid medium 1 from different directions are used. For reasons of simplicity, these elements of the device for imaging the interior of a turbid medium are only schematically indicated in FIG. 2. In FIG. 2, the control unit 8 comprises the light source 6 and the plurality of detectors 7. For example, in the device according to the embodiment, 256 different source positions are provided and 256 detector positions, i.e. respective ends of light guides are provided on the inner surface of the receptacle 2. The light from the light source 6 is subsequently directed to the turbid medium 1 from the 256 source positions and for each source position, the light emanating from the turbid medium 1 is detected in the 256 detection positions. However, the invention is not limited to these specific numbers.

The size of the receptacle 2 is such that a space remains between the inner surface of the receptacle 2 and the turbid medium 1. For examination, this space is filled with an optically matching medium 4 which serves to provide optical coupling between the turbid medium 1 to be imaged and the inner surface of the receptacle 2. The optically matching medium 4 further serves to prevent optical short-cutting between the light guides 5 coming from the light source 6 and the light guides 5 coupling to the detectors 7. Furthermore, the optically matching medium 4 serves to counteract boundary effects in the reconstructed image which are caused by the difference in optical contrast between the interior of the turbid medium 1 and the remaining space in the receptacle 2. For this purpose, the optically matching medium 4 is provided with optical properties which substantially match the optical properties of the turbid medium 1 to be examined.

The device is particularly adapted for optical fluorescence tomography in which a fluorescent contrast agent is used which, prior to examination, is injected into the turbid medium 1 to be examined and accumulates in cancer cells.

In the conventional methods for reconstructing an image of the interior of the turbid medium, before the actual measurement is performed, a reference measurement is performed with the receptacle 2 completely filled with the optically matching medium 4 and without turbid medium 1 placed in the receptacle. In the actual measurement, the turbid medium 1 to be examined is placed in the receptacle 2 and the measurement is performed. It is then assumed that the turbid medium 1 forms only small "perturbations" as compared to the reference measurement in which only the optically matching medium 4 is present in the receptacle 2, and the first order Born approximation is used for reconstructing the image of the interior of the turbid medium 1, meaning that the influence on the signal owing to a particular inhomogeneity in the medium does not interfere with the signal change owing to another inhomogeneity, i.e. all influences can be added linearly.

However, it has been found that the first order Born approximation does not hold in case of diffuse optical tomography (DOT) of breast tissue. This can be inferred from the following: In reconstructing the image, a forward calculation is performed and the (expected) photon density $\Phi$ is calculated ($\Phi_{calc}$) using a best guess of the image and solving the diffusion equation. The result is compared to the value of a measurement of the photon density $\Phi$ ($\Phi_{meas}$) for all the source-detector combinations (for further details on the reconstruction it is referred to the prior art cited above in the introductory part). The following error function $\chi$, with N being the number of source-detector combinations and the summation performed over all combinations:

$$\chi = \sqrt{\frac{\sum_n (\Phi_{n,calc} - \Phi_{n,meas})}{N(N-1)}}$$

describes how well the measurement ($\Phi_{meas}$) and the calculation ($\Phi_{calc}$) correspond to each other. In operation, if $\chi$ is large, the image is updated and a new forward calculation is started. At the end of this iterative process, the value of the error function should be substantially the same as the inaccuracy of a measurement. For phantoms, i.e. artificial tissue material with similar optical properties as real tissue, constructed from a homogeneous turbid medium with a finite number (e.g. three) of small objects this is true. However, for in-vivo measurements of breast tissue the error function of all the reconstructions using the Born approximation has been found to be about 10 times larger than the measurement inaccuracy. Thus, the conventional method does not fulfill the assumption that linear approximation is sufficient for solving the problem. The reconstruction problem which has to be solved when using the reference measurement with only the optically matching medium 4 and the actual measurement with the turbid medium 1 placed in the receptacle 2 deserves often a higher order perturbation approach.

A non-linear problem can be linearized by considering that only small differences to a certain steady-state solution have occurred. However, in particular with respect to diffuse optical tomography of in-vivo breast tissue this is difficult, since the comparison of measurements on the turbid medium without lesions to those of the turbid medium with lesions is not possible.

However, according to the embodiments, a way is provided to linearize the problem such that the first order Born approximation leads to satisfactory results. This is achieved by providing a reference measurement and an actual measurement, wherein the spatial perturbation of $\mu_s'$ and $\mu_a$ is small in the actual measurement as compared to the reference measurement.

First Embodiment

According to a first embodiment, a fluorescent contrast agent which tends to accumulate in cancer cells is used during examination of the turbid medium 1. For example, the fluorescent contrast agent SF64 by Bayer Schering Pharma is injected into the tissue under examination. The contrast agent accumulates to a higher concentration in lesions than in normal, healthy tissue owing to, among others, a higher degree of vascularization in and around a lesion. Further, in a turbid medium 1 such as a female human breast, the take-up and wash-out of the contrast agent by various structures inside the turbid medium 1 will take place at different time scales. The concentration of the fluorescent contrast agent will decay more slowly at the site of a lesion as compared to normal, healthy tissue. Thus, in the embodiment the fact is used that diseased tissue has a different wash-out time as compared to healthy tissue.

According to the first embodiment, the turbid medium 1 to which the contrast agent has been administered is placed in the receptacle 2 of the device for examining turbid media. First, after injecting the patient with the fluorescent contrast agent, one waits longer than the time it takes until the concentration has reached its highest value. During the wash-out (decay) of the contrast agent from the turbid medium 1, two measurements are performed at two well-separated times $t_1$ and $t_2$. The time interval $\Delta t$ ($\Delta t = t_2 - t_1$) is chosen such that it is on the order of the decay time of the concentration of the contrast agent.

Next, an averaged term (average multiplier) $\langle M \rangle$ is calculated according to the following equation:

$$\langle M \rangle = \frac{1}{N} \sum_{n=1,\ldots,N} \frac{\Phi_n(t_1)}{\Phi_n(t_2)}$$

wherein the summation is taken over all N source-detector combinations and $\Phi_n$ are the respective normalized detected photon densities for these source-detector combinations. This averaged term is an exponential function of the averaged decay constant $\tau$ of the concentration of the contrast agent, i.e. $\exp[(t_2-t_1)/\tau]$. It should be noted that e.g. exact photon fluxes can be measured by appropriately calibrated detectors. However, voltage or current values output by the detectors can also be directly used, as will become apparent from the following. Now a new merit function ($\Delta\Phi_{fluor}/\Phi$) is defined as follows:

$$\left(\frac{\Delta\Phi_{fluor}}{\Phi}\right)_n = 1 - \langle M \rangle \frac{\Phi_n(t_2)}{\Phi_n(t_1)} = 1 - \frac{\langle M \rangle}{M_n}$$

with $M_n = \Phi_n(t_1)/\Phi_n(t_2)$. This merit function is calculated for all N source-detector combinations. By definition, the merit function is on average zero. Moreover, it is normalized. Differences in source strength or detector sensitivity are automatically calibrated. Only small deviations from zero will be present owing to the relatively small volume of lesions in comparison to the total turbid medium. This new merit function fulfills all the properties of linear perturbation. Therefore, an image reconstruction based on this merit function using the linear Born approximation can be applied. For example, in a simple approach the merit function according to the equation above is used as input to a standard backprojection algorithm as is used in X-ray tomography. A more sophisticated image reconstruction can e.g. use the average values of the turbid medium for absorption and scattering coefficients and calculate the average photon density for a given source detector pair. In this approach, subsequently, the values of absorption and scattering are position dependent updated to account for the small deviations in the merit function. As a consequence, an image of the interior of a turbid medium can be reconstructed with satisfactory accuracy using linear approximation.

It should be noted that the times $t_1$ and $t_2$ should differ enough in all embodiments to get a meaningful value for the multiplier and thus the merit function.

It should be noted that, according to the embodiment, no two images of the interior of the turbid medium are reconstructed which are thereafter compared. To the contrary, the measurement results, i.e. the detected values, are directly used. Thus, the detected values of the first measurement are directly used as a reference for the detected values of the second measurement. The current invention references the direct measurement at time $t_1$ with a similar measurement on the same medium at time $t_2$ before image reconstruction.

Second Embodiment

According to a second embodiment, no fluorescent contrast agent is used. Instead of fluorescence other contrast mechanisms may apply, such as the variation of applied pressure to the turbid medium, the injection of an optically absorbing contrast agent or the difference between the tissue properties during exhaling or inhaling of the breath. At a certain point in time a first measurement for imaging the interior of a turbid medium is performed. For this first measurement, the turbid medium 1 to be examined, e.g. a breast, is placed in the receptacle 2 of the device and a scan in which the light is directed to the turbid medium 1 from different directions is performed. The signals detected by the plurality of detectors 7 are sampled and stored. The results of this measurement, i.e. the set of data generated in this first measurement is then stored for example in a storage in the device for imaging turbid media or in the storage of a personal computer. A second measurement is performed exactly in the same way as the first measurement, e.g. after applying pressure or after waiting half a breathing cycle. Again, the results of this measurement are stored in the storage.

For reconstructing an image of the interior of the turbid medium 1, the results of the first measurement are used as a reference for the results of the second measurement. Relative to the reference measurement the differences in the optical properties of the examined turbid medium 1 will be small in the second measurement, e.g. when the turbid medium 1 is a female human breast and imaging is performed for identifying and/or observing breast tumors. Thus, as a consequence only slight deviations in the set of data from the second measurement will be present as compared to the reference measurement such that a linear reconstruction problem is given and the conditions for applying the first order Born approximation are fulfilled. Then, according to the second embodiment a merit function is calculated similar to that described with respect to the first embodiment and the merit function is used for reconstructing an image of the interior of the turbid medium.

MODIFICATIONS

For all embodiments, a more subtle approach can be undertaken, by making a histogram of the ratio's of all measurements at time $t_1$ and $t_2$ for all source-detector combinations in stead of making a single average. This approach will be described with reference to FIG. 3.

Figure 3:
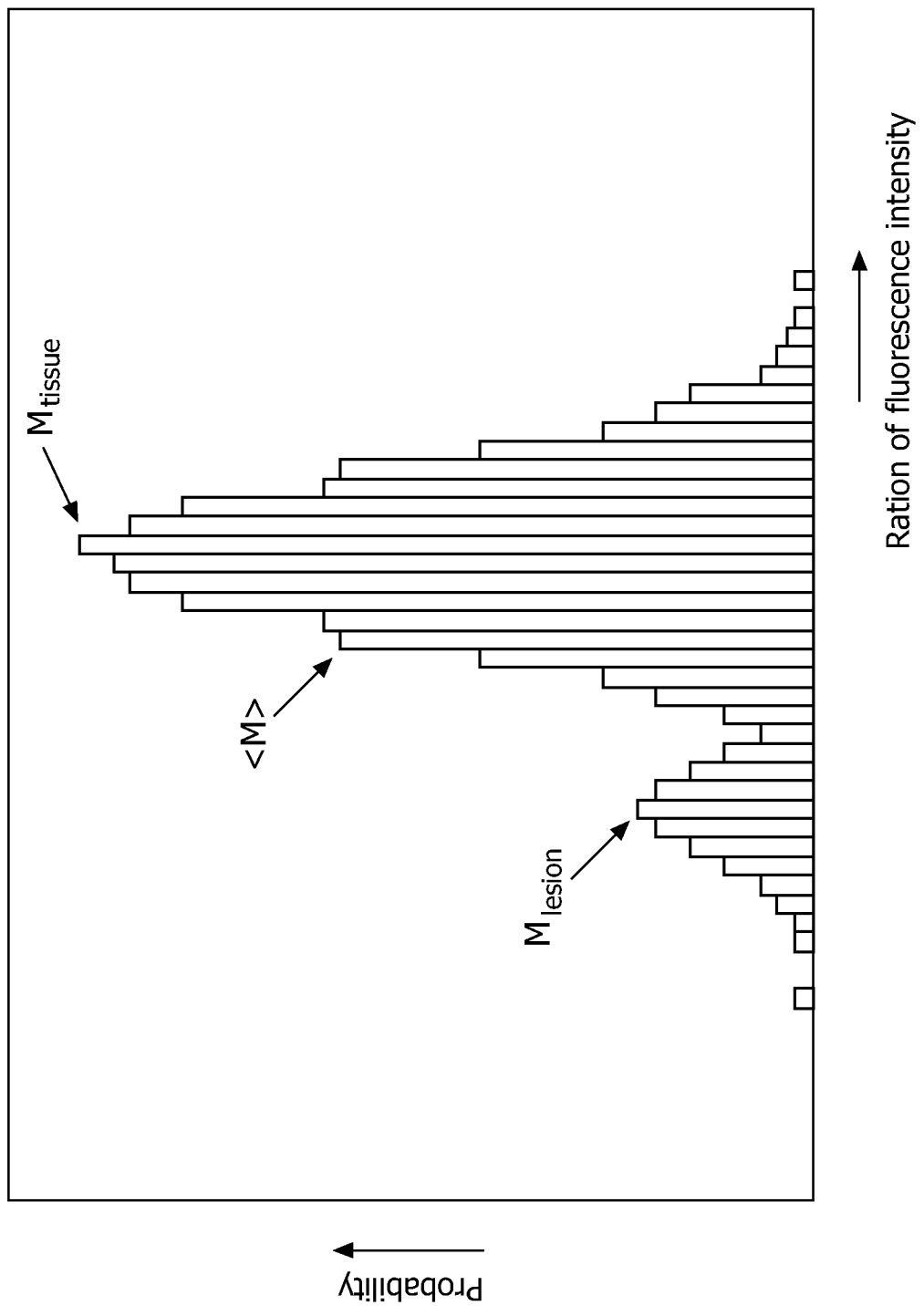
FIG. 3 shows a histogram used for detecting the presence of inhomogeneities according to a modification.

According to the modification, a histogram of the ratios of all measurements at the times $t_1$ and $t_2$ for all source-detector combinations is made. In other words: the ratio of the first and second measurements is plotted for all source-detector pairs versus the frequency of occurrence (designated as probability) of a specific ratio, as shown in FIG. 3. This means, the ratio $M_n = \Phi_n(t_1)/\Phi_n(t_2)$ is calculated for all N source-detector combinations from the measured results. Then, a graph is created with the specific ratios $M_n$, on the x-axis and the number of occurrences of the specific ratios, i.e. the number of source-detector pairs providing the specific ratios, on the y-axis. Thus, the y-axis is related to the probability of occurrence of a certain ratio. Normal healthy tissue will lead to maximum in the graph for a specific value of $M_n$, with a Gaussian distribution around this maximum. Those measurements of source-detector combinations with a contribution of a lesion or other inhomogeneity of a certain degree will exhibit a smaller ratio and will cause a deviation from a normal Gaussian distribution which will show as a further maximum ($M_{lesion}$) at a smaller ratio. In this way, the presence of a lesion or other inhomogeneity can be seen even before a full reconstruction has been performed. By observing the source detector pair combinations that deviate from the Gaussian distribution, the position of an inhomogeneity can be inferred, since all the lines from source to detector of those combination should run through this inhomogeneity.

However, the results achieved by providing the histogram can also be used for later image reconstruction. According to this further possibility, instead of taking the first moment of the distribution, i.e. the average multiplier <M>, the position of the maximum $M_{tissue}$ in the histogram (see FIG. 3) corresponding to normal healthy tissue is taken as the value for the multiplier instead of using <M> in the equation described with respect to the first embodiment. The resulting merit function is used for the reconstruction in quite an analogous way.

The merit function described above with respect to the first and second embodiments is based on the first order derivative of the measured signals with respect to time. However, in a further modification the merit function could be based on a higher order derivative, e.g. the second order derivative. In case of the second order, the following merit function ($\Delta\Phi_2/\Phi$) results:

$$\left(\frac{\Delta\Phi_2}{\Phi}\right)_n = \frac{\Phi_n(t_1) - 2<M_{12}>\Phi_n(t_2) + <M_{23}>\Phi_n(t_3)}{\Phi_n(t_1)} \text{ with } t_1 < t_2 < t_3$$

where <$M_{12}$> and <$M_{23}$> are the average ratios of measurements at the corresponding time intervals. The average is taken over all source detector combinations in the following way:

$$\langle M_{12}\rangle = \frac{1}{N}\sum_{n=1,\ldots,N}\frac{\Phi_n(t_1)}{\Phi_n(t_2)}$$

$$\langle M_{23}\rangle = \frac{1}{N}\sum_{n=1,\ldots,N}\frac{\Phi_n(t_2)}{\Phi_n(t_3)}$$

It could be considered that the embodiments and their modifications have the disadvantage that positions of the turbid medium 1 in the receptacle 2 are different in the first and second measurements. This could be due to the fact that, in the second embodiment, the turbid medium 1 has been removed from the receptacle 2 and again placed therein or, in the first embodiment, the turbid medium 1 has been moved, e.g. by movement of the woman in case of in-vivo mammography. In the first embodiment, in case of optical mammography the difference between the measurements will be minutes or tens of minutes. However, for a realistic example implementation of the embodiment described above, for example the image resolution will be 2.5 mm (cubic root of the receptacle volume divided by the number of source-detector pairs) if no measurement errors are present and the reconstruction is flawless. Since neither of these two conditions will be true, the reproducibility of the position of the turbid medium 1 in the receptacle 2 should be on the order of 5-10 mm which can be easily achieved.

Although specific embodiments have been described above, the invention is not limited to those embodiments. Although the receiving volume has been described as a receptacle having a cup-like shape, it is not limited thereto. It may have other suitable shapes. In particular, a combination of features of the embodiments and modifications thereof is possible.

The invention claimed is:

1. Method for detecting the presence of inhomogeneities in an interior of a turbid medium, the method comprising the steps:
    performing a first measurement with the turbid medium to be examined in a receiving volume of a device for examining the interior of turbid media;
    performing a second measurement with the turbid medium to be examined in the receiving volume of the device for examining the interior of turbid media, wherein the second measurement is performed after a time interval has passed after the first measurement;
    each of the first and second measurements comprising:
        irradiating the turbid medium with light from a light source wherein the light from the light source irradiates the turbid medium from a plurality of different source positions, and further wherein the light from the light source irradiates the turbid medium without combining with light from any other source,
            and for each source position, detecting light emanating from the turbid medium in a plurality of different detection positions, and
        storing the detected values as measurement results; and
    detecting inhomogeneities in the interior of the turbid medium by using the measurement results of one of the first and second measurements as a reference and the measurement results of the respective other of the first and second measurements to determine deviations from the reference, wherein a multiplier for detecting inhomogenities is calculated, and further wherein computing the multipler comprises, for each combination of a source position and a detection position:
    computing a ratio between the measurement result from one of the first and second measurements and the corresponding measurement result from the respective other of the first and second measurements,
    wherein an averaged term <M> is computed according to the equation:

$$\langle M\rangle = \frac{1}{N}\sum_n \frac{\Phi_n(t_1)}{\Phi_n(t_2)}$$

with N being the number of different combinations of source positions and detection positions, n being an index for specific combinations of the source positions and the detection positions, $\Phi$ being the detected photon density, $t_1$ being the time of the first measurement, and $t_2$ being the time of the second measurement.

2. The method according to claim 1, wherein an image of the interior of the turbid medium is reconstructed based on the measurement results of the first and second measurements.

3. The method according to claim 2, wherein a first order Born approximation is used for reconstructing the image of the interior of the turbid medium.

4. The method according to claim 1, wherein the presence of an inhomogeneity is detected by generating a histogram based on the measurement results of the first and second measurements.

5. The method according to claim 1, wherein the first measurement and the second measurement are performed over a time interval where an oxygenation level and/or blood content in the turbid medium has changed based on a variation in applied pressure or based on differences within an inhale/exhale breathing cycle.

6. The method according to claim 1, wherein a contrast agent is injected into the turbid medium before the first measurement is performed and the time interval between the first and second measurements is chosen based on a decay time of the contrast agent.

7. A device for detecting the presence of inhomogeneities in the interior of turbid media, the device comprising:
    a receiving volume configured to receive a turbid medium to be examined;
    a light source configured to irradiate an interior of the receiving volume;
    at least one detector configured to detect light emanating from the interior of the receiving volume; and
    a control unit configured to control the device for imaging the interior of turbid media;
    wherein the control unit is further configured to control the device for imaging the interior of turbid media such that:
    a first measurement with a turbid medium placed in the receiving volume is performed, and
    a second measurement with the turbid medium placed in the receiving volume is performed after a time interval has passed after the first measurement,
    in each of the first and second measurements the turbid medium is subsequently irradiated with light from the light source wherein the light from the light source irradiates the turbid medium from a plurality of different source positions, and further wherein the light from the light source irradiates the turbid medium without combining with light from any other source,
    and, for each source position, light emanating from the turbid medium is detected in a plurality of different detection positions by the at least one detector, and the detected values are stored as measurement results;
wherein the control unit is further adapted such that:
the presence of inhomogeneities in the interior of the turbid medium is detected using the measurement results of one of the first and second measurements as a reference and the measurement results of the respective other of the first and second measurements to determine deviations from the reference, wherein a multiplier for detecting inhomogenities is calculated, and further wherein computing the multipler comprises, for each combination of a source position and a detection position:
computing a ratio between the measurement result from one of the first and second measurements and the corresponding measurement result from the respective other of the first and second measurements,
wherein an averaged term <M> is computed according to the equation:

$$\langle M \rangle = \frac{1}{N} \sum_n \frac{\Phi_n(t_1)}{\Phi_n(t_2)}$$

with N being the number of different combinations of source positions and detection positions, n being an index for specific combinations of the source positions and the detection positions, $\Phi$ being the detected photon density, $t_1$ being the time of the first measurement, and $t_2$ being the time of the second measurement.

8. The device according to claim 7, wherein the control unit is adapted such that an image of the interior of the turbid medium is reconstructed based on the measurement results of the first and second measurements.

9. The device according to claim 7, wherein the control unit is adapted to provide a histogram based on the measurement results of the first and second measurements for detecting the presence of inhomogeneities.

10. The device according to claim 7, wherein the device is a medical image acquisition device.

* * * * *